(12) United States Patent
Knoblich

(10) Patent No.: US 6,579,237 B1
(45) Date of Patent: Jun. 17, 2003

(54) DIAGNOSTIC ULTRASONIC IMAGING SYSTEM HAVING ORGANIC LIGHT EMITTING DEVICE DISPLAY

(75) Inventor: Stan Knoblich, Everett, WA (US)

(73) Assignee: Koninklijke Philips Electronics NV, Eindhoven (NL)

( * ) Notice: Subject to any disclaimer, the term of this patent is extended or adjusted under 35 U.S.C. 154(b) by 0 days.

(21) Appl. No.: 10/022,261

(22) Filed: Dec. 14, 2001

(51) Int. Cl.$^7$ .................................................. A61B 8/00
(52) U.S. Cl. ....................................................... 600/437
(58) Field of Search ................................ 600/437, 441, 600/443, 447; 349/202

(56) References Cited

U.S. PATENT DOCUMENTS

| | | | |
|---|---|---|---|
| 5,688,551 A | 11/1997 | Littman et al. ................ | 427/64 |
| 5,690,114 A * | 11/1997 | Chiang et al. ............... | 600/447 |
| 5,838,416 A * | 11/1998 | Chen et al. .................. | 349/202 |
| 5,920,080 A | 7/1999 | Jones .......................... | 257/40 |
| 5,924,988 A * | 7/1999 | Burris et al. ................. | 600/437 |
| 5,929,474 A | 7/1999 | Huang et al. ................ | 257/292 |
| 6,048,573 A | 4/2000 | Tang et al. .................... | 427/66 |
| 6,066,357 A | 5/2000 | Tang et al. .................... | 427/66 |
| 6,069,443 A | 5/2000 | Jones et al. .................. | 313/504 |
| 6,117,529 A | 9/2000 | Leising et al. ............... | 428/209 |
| 6,191,433 B1 | 2/2001 | Roitman et al. .............. | 257/40 |
| 6,210,814 B1 | 4/2001 | Thompson et al. ......... | 428/690 |
| 6,274,979 B1 | 8/2001 | Celii et al. .................. | 313/506 |
| 6,319,201 B1 * | 11/2001 | Wilk ........................... | 600/437 |

OTHER PUBLICATIONS

Anonymous, "UDC Wins $1 Million DARPA Program to Develop Flexible OLED Display", (visited Dec. 4, 2001) <http://www.businesswire.com/webbox/bw.062200/201742456.htm>.

* cited by examiner

*Primary Examiner*—Marvin M. Lateef
*Assistant Examiner*—Ruby Jain
(74) *Attorney, Agent, or Firm*—Dorsey & Whitney LLP

(57) ABSTRACT

A diagnostic ultrasonic imaging system includes an ultrasonic scanhead, an ultrasonic system chassis, and an organic light emitting device ("OLED") display. The OLED display has a response time of less than 10 ms, a contrast ratio of at least 1000:1, and a horizontal and vertical viewing angle of at least 160 degrees.

26 Claims, 3 Drawing Sheets

DIAGNOSTIC ULTRASONIC IMAGING SYSTEM HAVING ORGANIC LIGHT EMITTING DEVICE DISPLAY

TECHNICAL FIELD

This invention relates to diagnostic ultrasonic imaging systems, and more particularly, to diagnostic ultrasonic imaging systems displays that are optimally suited to displaying ultrasonic images.

BACKGROUND OF THE INVENTION

Diagnostic ultrasonic imaging systems are commonly used to image a wide variety of organs and tissues within the human body. A typical ultrasonic imaging system 10 is shown in FIG. 1. The imaging system 10 includes an ultrasonic scanhead 14 that is adapted to be placed in contact with a portion of a body that is to be imaged. The scanhead 14 is coupled to a system chassis 16 by a cable 18. The system chassis 16, which is mounted on a cart 20, includes a keyboard 24 by which data may be entered into a processor (not shown) that is included in the system chassis 16. A display, which may be a cathode ray tube ("CRT") display or a flat panel display 30 having a viewing screen 34, is placed on an upper surface of the system chassis 16. Such flat panel displays 30, such as liquid crystal displays ("LCD"), have been proposed for use in ultrasonic imaging system in, for example, U.S. Pat. No. 5,924,988 to Burris et al., which describes significant advantages that can be achieved by using a relatively thin and lightweight flat panel display.

The images displayed by conventional ultrasonic imaging systems have, in the past, been somewhat static. However, with the development of faster ultrasonic processors, it is possible to display real-time ultrasonic images of rapidly moving tissues and organs, such as a beating heart. However, it has been discovered that flat panel displays, such as liquid crystal displays, suggested for use in, for example, the above-cited patent to Burris et al., cannot optimally portray rapidly moving tissues and organs. This inability is due primarily to the relatively slow response times of conventional flat panel displays proposed for use in ultrasonic imaging systems. Thus, although the small size and light weight of flat panel displays proposed for use in ultrasonic imaging systems would provide many advantages, these advantages can be achieved only by sacrificing the ability to optimally display rapidly moving images.

Another problem that has been discovered with the use of flat panel displays proposed for use in ultrasonic monitoring systems is their lack of dynamic range or contrast ratio. It is often important to be able to discern subtle variations in the intensity of ultrasonic images. For example, it can be important to be able to differentiate an area reflecting substantially no ultrasonic energy, which should appear black, from an area reflecting a slight amount of ultrasonic energy, which should appear almost black. An ultrasonic image displayed on a flat panel display screen with insufficient dynamic range or contrast ratio will be unable to show the area reflecting substantially no ultrasonic energy darkly enough to differentiate that area from the area reflecting a slight amount of ultrasonic energy.

In addition to having a fast response time and a large dynamic range, a flat panel display used to view images in an ultrasonic imaging system should also have a wide viewing angle. The display of an ultrasonic imaging system is often mounted on a cart, but the sonographer or other health care practitioner is often positioned off to the side of the cart next to a patient. Unless the display for the ultrasonic imaging system can be viewed from the side, it may be difficult for the health care practitioner to view the ultrasonic image without taking his or her attention away from the patient. Furthermore, even within the viewing angle of flat panel displays proposed for use in ultrasonic imaging, the color or brightness of the image can vary substantially as the viewing angle is varied.

A need therefore exists for an ultrasonic imaging system having a display that has a response time sufficiently short to display rapidly moving images, a dynamic range or contrast ratio sufficient to discern slight variations in the intensity of ultrasonic echoes, and a view angle that is sufficiently wide that the display can be easily viewed by a health care practitioner while devoting sufficient attention to a patient being examined.

SUMMARY OF THE INVENTION

An ultrasonic imaging system includes a system chassis, an ultrasonic scanhead coupled to the system chassis, and an organic light emitting device display coupled to the system chassis. The display includes a viewing screen on which an ultrasonic image can be displayed with superior response times, contrast ratios, and viewing angles. The response time of the organic light emitting device display is preferably less than 10 ms, and more preferably less than 1 ms. The contrast ratio of the organic light emitting device display is preferably at least 1000:1, and more preferably at least 4000:1. The horizontal and vertical viewing angle of the organic light emitting device display is preferably at least 160 degrees, and more preferably at least 180 degrees.

DETAILED DESCRIPTION OF THE INVENTION

Figure 1:
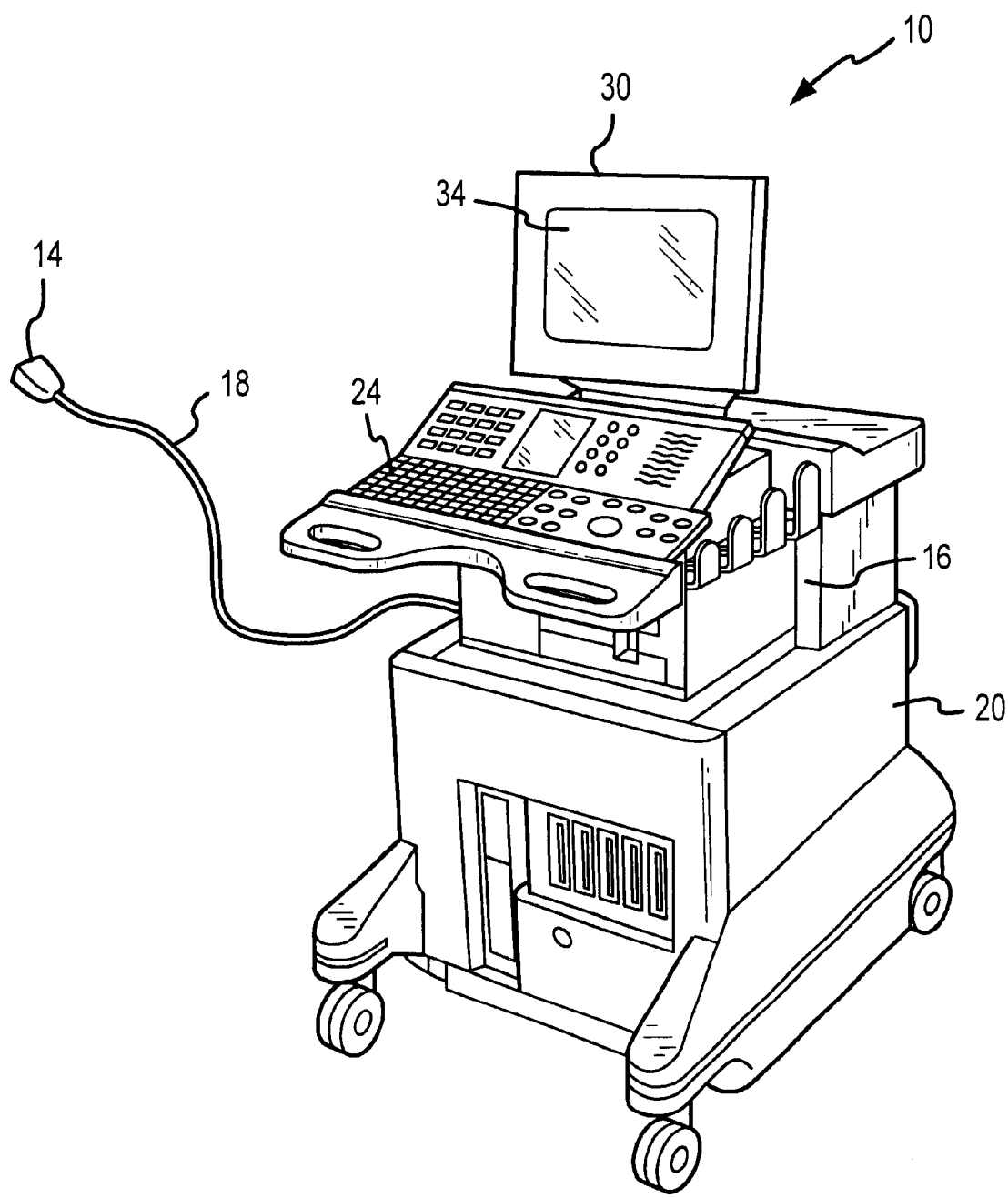
FIG. 1 is an isometric view of a typical prior art cart-mounted diagnostic ultrasonic imaging system.
Figure 2:
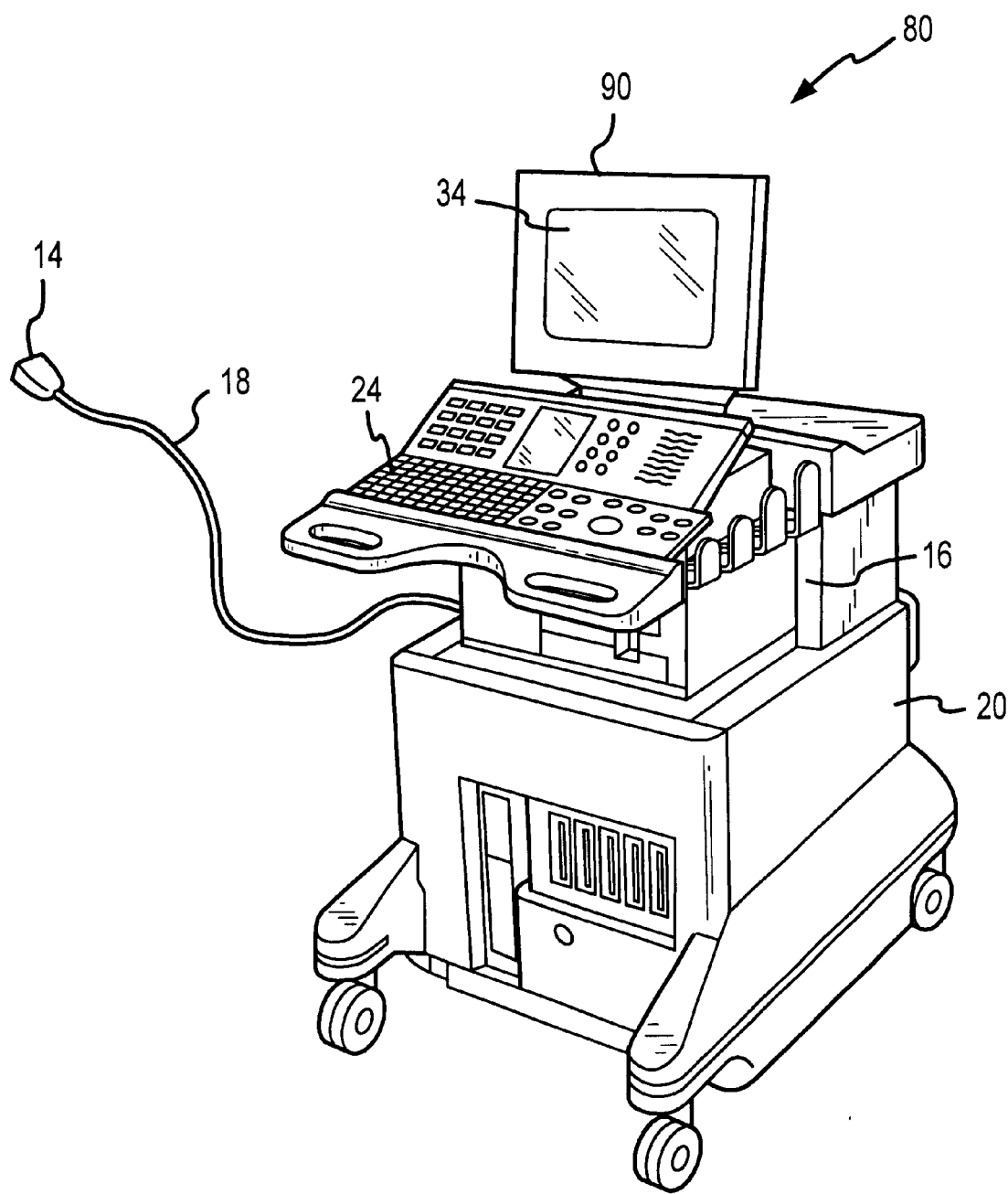
FIG. 2 is an isometric view of a cart-mounted diagnostic ultrasonic imaging system using an organic light emitting device ("OLED") display according to one embodiment of the invention.

An ultrasonic imaging system 80 in accordance with one embodiment of the invention is shown in FIG. 2. The ultrasonic imaging system 80 uses most of the same components as the imaging system 10 of FIG. 1. Therefore, in the interest of brevity, these components have been provided with the same reference numerals, and an explanation of their operation will not be repeated. The imaging system 80 differs from the imaging system 10 of FIG. 1 in the use of an organic light emitting device ("OLED") display 90. OLED displays are described in, for example, U.S. Pat. Nos. 5,920,080; 5,929,474; 6,069,443; 6,117,529; 6,191,433; 6,210,814; and 6,274,979, all of which are incorporated herein by reference. As described in detail below, the OLED display 90 provides the ultrasonic imaging system 80 with several advantages over the prior art imaging system 10 having a flat panel display 30, as shown in FIG. 1. The OLED display 90 used in the ultrasonic imaging system 80 is a color OLED display. However, it will be understood that the OLED display 90 may alternatively be a monochrome OLED display or an OLED display having a limited range of colors.

OLED displays, such as the OLED display 90 shown in FIG. 2, have a relatively short response time. For example compared with convention LCD flat panel displays, which typically have a response time greater than 20–50 ms, OLED displays have response times less than 1 ms. The OLED display 90 used in the ultrasonic imaging system 80 preferably has a response time of less than 10 ms, and more preferably a response time of less than 1 ms. As a result, the OLED display 90 is able to portray real time images of rapidly moving tissues and organs with significantly greater clarity than the conventional flat panel display 30 proposed for use in ultrasonic imaging systems.

The OLED display 90 also has a significantly wider dynamic range or contrast ratio than the flat panel display 30 shown in FIG. 1. As a result, it is possible to discern subtle differences in brightness of ultrasonic images shown in the display 90 compared to the ultrasonic imaging system 10 of FIG. 1. In part, this increased dynamic range is due to the degree of "blackness" that the display 90 is capable of generating in areas of the displayed image corresponding to areas from which little or no ultrasonic echoes are received. In one embodiment of the ultrasonic imaging system 80, the OLED display 90 has a contrast ratio of at least 1,000:1, and preferably a contrast ratio of at least 4,000:1.

The OLED display 90 used in the ultrasonic imaging system 80 of FIG. 2 also has the advantage of a wide viewing angle compared to the flat panel display 30 used in the ultrasonic imaging system 10 of FIG. 1. In one embodiment, the OLED display 90 used in the imaging system 80 has a horizontal and vertical viewing angle of at least 160 degrees and, preferably a horizontal and vertical viewing angle of at least 180 degrees. If the OLED display is fabricated on a curved or flexible substrate, viewing angles in excess of 180 degrees are possible, such as viewing angles of 200 degrees. Within these viewing angles, an ultrasonic image presented on the display 90 can not only be viewed, but it can be viewed without substantial shifts in color or brightness as the viewing angle is varied. In contrast, the flat panel display 30, such as an LCD display, used in the ultrasonic imaging system 10 typically has a horizontal and vertical viewing angle of no more than 160 degrees, and, within this viewing angle, the color and brightness of the displayed image can shift substantially as the viewing angle is varied. As a result, a sonographer or other health care practitioner can view a good quality image on the display 90 with relative ease while devoting adequate attention to a patient being examined.

Figure 3:
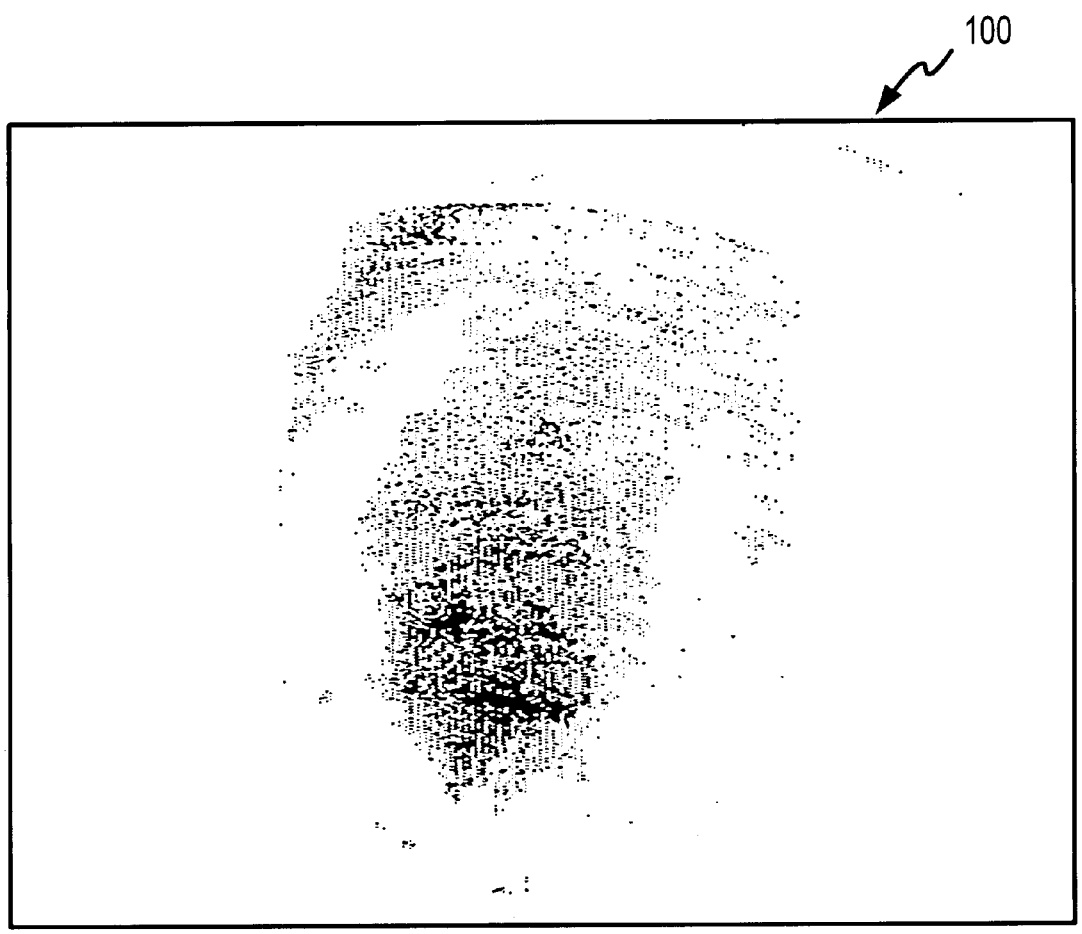
FIG. 3 is a screen shot of an ultrasonic image displayed using the diagnostic ultrasonic imaging system of FIG. 2.

An example of an ultrasonic image 100 that may be generated using the ultrasonic imaging system 80 is shown in FIG. 3. The image 100 is of a heart of an infant, which, as is known in the art, often beats very rapidly compared to the heart rate of an adult. As a result, the heart moves rapidly commensurate with this rapid heart beat. Despite the rapid heart beat, the image 100 is clearly shown because of the rapid response time, i.e., under 1 ms, of the OLED display 90 used in the system 80. Furthermore, although not readily apparent in FIG. 3 because of the limitations on graphic rendering, subtle differences in the intensity of the image 100 can be discerned because the image has a contrast ratio of at least 1000:1 made possible by the high contrast ratio capabilities of the OLED display 90. Finally, although also not apparent from FIG. 3, the horizontal and vertical viewing angle of the image 100 is at least 160 degrees and preferably up to 180 degrees.

While FIG. 2 illustrates the OLED display 90 in use with a cart-borne ultrasound system, it will be appreciated that the OLED display 90 is also well suited for use with smaller, more portable ultrasound systems and ultrasound image viewing devices where the small size and light weight of the OLED display provides significant advantage. For example, the OLED display 90 may be used with a desktop, hand-carried, and handheld ultrasound systems, as well as with workstations for viewing and manipulating ultrasound images.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An ultrasonic imaging system, comprising:
    a system chassis;
    an ultrasonic scanhead coupled to the system chassis; and
    an organic light emitting device display coupled to the system chassis, the display having a viewing screen on which an ultrasonic image can be displayed.

2. The ultrasonic imaging system of claim 1, wherein the organic light emitting device display has a response time of less than 10 ms.

3. The ultrasonic imaging system of claim 2, wherein the organic light emitting device display has a response time of less than 1 ms.

4. The ultrasonic imaging system of claim 1, wherein the organic light emitting device display has a contrast ratio of at least 1000:1.

5. The ultrasonic imaging system of claim 4, wherein the organic light emitting device display has a contrast ratio of at least 2000:1.

6. The ultrasonic imaging system of claim 1, wherein the organic light emitting device display has a horizontal and vertical viewing angle of at least 160 degrees.

7. The ultrasonic imaging system of claim 6, wherein the organic light emitting device display has a horizontal and vertical viewing angle of at least 180 degrees.

8. The ultrasonic imaging system of claim 1, wherein the organic light emitting device display comprises a color organic light emitting device display.

9. An ultrasonic imaging system, comprising:
    a system chassis;
    an ultrasonic scanhead coupled to the system chassis; and
    a flat panel display coupled to the system chassis, the flat panel display having a viewing screen on which an ultrasonic image can be displayed, the flat panel display having a response time of less than 10 ms.

10. The ultrasonic imaging system of claim 9, wherein the flat panel display comprises a flat panel display having a response time of less than 1 ms.

11. The ultrasonic imaging system of claim 9, wherein the flat panel display comprises an organic light emitting device display.

12. The ultrasonic imaging system of claim 11, wherein the organic light emitting device display comprises a color organic light emitting device display.

13. An ultrasonic imaging system, comprising:
    a ultrasound image processor; and
    an organic light emitting device display coupled to the system chassis, the display having a viewing screen on which an ultrasonic image can be displayed.

14. The ultrasonic imaging system of claim 13, wherein the ultrasound image processor comprises a desktop unit.

15. The ultrasonic imaging system of claim 13, wherein the ultrasound image processor comprises a diagnostic image workstation.

16. An ultrasonic imaging system, comprising:

a system chassis;

an ultrasonic scanhead coupled to the system chassis; and a flat panel display coupled to the system chassis, the flat panel display having a viewing screen on which an ultrasonic image can be displayed, the flat panel display having a horizontal and vertical viewing angle of at least 160 degrees.

17. The ultrasonic imaging system of claim 16, wherein the flat panel display comprises a flat panel display having a horizontal and vertical viewing angle of at least 180 degrees.

18. The ultrasonic imaging system of claim 16, wherein the flat panel display comprises an organic light emitting device display.

19. The ultrasonic imaging system of claim 18, wherein the organic light emitting device display comprises a color organic light emitting device display.

20. A diagnostic ultrasonic image of an object, the image being shown with a response time of less than 10 ms, a contrast ratio of at least 1000:1 and a horizontal and vertical viewing angle of at least 160 degrees.

21. The diagnostic ultrasonic image of claim 20, wherein the image is shown with a response time of less than 1 ms, a contrast ratio of at least 4000:1 and a horizontal and vertical viewing angle of at least 200 degrees.

22. A method of displaying an ultrasonic image, comprising:

providing an ultrasonic imaging system, including an organic light emitting device display having a viewing screen;

obtaining data corresponding to an ultrasonic image; and displaying the ultrasonic image on the viewing screen of the organic light emitting device display.

23. The method of claim 22, wherein the act of providing an ultrasonic imaging system including an organic light emitting device display comprises providing an ultrasonic imaging system including a color organic light emitting device display.

24. The ultrasonic imaging system of claim 17, wherein the flat panel display comprises a flat panel display having a horizontal and vertical viewing angle of at least 200 degrees.

25. The ultrasonic imaging system of claim 25, wherein the flat panel display comprises a flat panel display having a horizontal and vertical viewing angle of at least 180 degrees.

26. The ultrasonic imaging system of claim 25, wherein the flat panel display comprises a flat panel display having a horizontal and vertical viewing angle of at least 200 degrees.

* * * * *

UNITED STATES PATENT AND TRADEMARK OFFICE
CERTIFICATE OF CORRECTION

PATENT NO. : 6,579,237 B1
DATED : June 17, 2003
INVENTOR(S) : Stan Knoblich

It is certified that error appears in the above-identified patent and that said Letters Patent is hereby corrected as shown below:

Title page,
Item [56], References Cited, OTHER PUBLICATIONS, "Anonymous" reference, reads "OLED Display", visited" should read -- OLED Display" (visited --

Column 1,
Line 29, reads "system in, for example," should read -- systems in, for example, --

Column 2,
Lines 57-58, reads "5,920,080; 5,929,474; 6,069,443; 6,117,529; 6,191,433; 6,210,814; and" should read -- 5,920,080, 5,929,474, 6,069,443, 6,117,529, 6,191,433, 6,210,814 and --

Column 6,
Line 18, reads "system of claim 25, "wherein" should read -- system of claim 20, wherein --

Signed and Sealed this

Eighteenth Day of May, 2004

JON W. DUDAS
*Acting Director of the United States Patent and Trademark Office*